(12) United States Patent
Bowman et al.

(10) Patent No.: US 10,842,607 B2
(45) Date of Patent: Nov. 24, 2020

(54) EMBOLIC COILS

(71) Applicant: MicroVention, Inc., Aliso Viejo, CA (US)

(72) Inventors: Heath Bowman, Trabuco Canyon, CA (US); Susanna Lin, Los Angeles, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 267 days.

(21) Appl. No.: 15/784,059

(22) Filed: Oct. 13, 2017

(65) Prior Publication Data

US 2018/0104040 A1 Apr. 19, 2018

Related U.S. Application Data

(60) Provisional application No. 62/408,263, filed on Oct. 14, 2016.

(51) Int. Cl.
*A61F 2/01* (2006.01)
*A61B 17/12* (2006.01)
*A61B 17/00* (2006.01)

(52) U.S. Cl.
CPC .......... *A61F 2/01* (2013.01); *A61B 17/12145* (2013.01); *A61B 2017/00526* (2013.01); *A61F 2002/016* (2013.01); *A61F 2230/0091* (2013.01); *A61F 2240/001* (2013.01)

(58) Field of Classification Search
CPC .......... A61B 17/12145; A61B 17/1214; A61F 2230/0091
See application file for complete search history.

(56) References Cited

U.S. PATENT DOCUMENTS

| | | | |
|---|---|---|---|
| 5,639,277 A | 6/1997 | Mariant et al. | |
| 5,649,949 A * | 7/1997 | Wallace | A61B 17/12022 600/200 |
| 5,749,891 A | 5/1998 | Ken et al. | |
| 5,951,599 A * | 9/1999 | McCrory | A61B 17/12022 606/108 |
| 6,322,576 B1 | 11/2001 | Wallace et al. | |
| 6,860,893 B2 * | 3/2005 | Wallace | A61B 17/12145 606/200 |
| 7,014,645 B2 | 3/2006 | Greene et al. | |
| 9,089,405 B1 | 7/2015 | Gulachenski et al. | |
| 2002/0052613 A1 * | 5/2002 | Ferrera | A61B 17/12022 606/157 |
| 2003/0018356 A1 | 1/2003 | Schaefer et al. | |
| 2004/0098028 A1 | 5/2004 | Martinez | |
| 2005/0192618 A1 | 9/2005 | Porter | |
| 2007/0175536 A1 | 8/2007 | Monetti et al. | |

* cited by examiner

*Primary Examiner* — Gregory A Anderson
(74) *Attorney, Agent, or Firm* — Inskeep IP Group, Inc.

(57) ABSTRACT

An embolic coil with a secondary, delivered shape utilizing regions of varying stiffness is described. In some embodiments, these regions of varying stiffness are created by utilizing a larger primary wind loop diameter to create selective regions with lower stiffness and higher flexibility. In some embodiments, these regions of higher flexibility correspond to inflection regions on a complex coil shape to ease deliverability of the coil during therapeutic procedures.

12 Claims, 3 Drawing Sheets

EMBOLIC COILS

RELATED APPLICATIONS

This application claims priority to U.S. Provisional Application Ser. No. 62/408,263 filed Oct. 14, 2006 entitled Embolic Coils, which is hereby incorporated herein by reference in its entirety.

BACKGROUND OF THE INVENTION

Embolic or vaso-occlusive coils are used for a variety of reasons within the vasculature, including in the treatment of aneurysms. When used to treat aneurysms, the coils are placed within the aneurysm to occlude the aneurysm and limit blood-flow to the aneurysm over time, thereby mitigating the risk of rupture and stroke.

Embolic coils are typically formed by creating a plurality of uniform, helical loops with a wire. Often, these coiled wires are then further wound on mandrels of various shapes and heat set to impart those shapes to the coil when unconstrained. When constrained in a catheter or delivery sheath, the embolic coil is constrained to an elongated orientation. But when removed from the catheter, the embolic coil bends or curves according to the shape that was heat set on. This secondary shape is often three-dimensional in nature, forming a number of different loops and shapes at different angles relative to each other. These shaped coils are often referred to as complex coils and can be useful for framing the periphery of the aneurysm, for filling the space of the aneurysm, or for other treatment purposes.

The complex coils may have a number of inflection or transition regions in areas of the coil where the wind direction changes. Delivery of complex coils can be problematic since the coils adopt their complex secondary shape after being released from the catheter and these inflection regions can create a kick or jump in both the coil and the delivery catheter. These kicks or jumps can result in the delivery catheter and/or coil being displaced from the target treatment site. Hence, there is a need for a complex coil which mitigates these issues.

SUMMARY OF THE INVENTION

An embolic or vaso-occlusive coil, method of making the coil, and method of using the coil is described.

In one embodiment, the embolic coil has a primary shape which includes helical loops having smaller diameter and larger diameter regions. The coil adopts its primary shape during delivery through a catheter. In one embodiment, these regions are placed in selective locations throughout the coil. In one embodiment, the larger primary-wind diameter regions correspond to particular positions in the secondary, complex shape of the coil. In one embodiment, an inflection region in the secondary, complex shape of the coil utilizes a larger primary-shape diameter to increase flexibility within the region. The coil adopts its secondary, complex shape after being released from the catheter.

In one embodiment, a primary shape is imparted into an embolic coil by winding the wire of the coil over a shaped mandrel with smaller diameter and larger diameter regions. The coil adopts its primary shape during delivery through a catheter. Another mandrel is then used to wind the embolic coil into a secondary, complex shape where selective portions of the secondary, complex shape correspond to larger diameter primary-wind sections. In one embodiment, inflection regions in the secondary, complex shape of the coil correspond to the larger diameter regions of the primary wind shape. The coil adopts its secondary, complex shape after being released from the catheter.

In one embodiment, a method of making an embolic coil involves winding a wire of a coil over a shaped mandrel with larger and smaller diameter regions to impart a primary shape into the embolic coil. The embolic coil is then wound over another mandrel to impart a secondary, complex shape where the larger diameter regions of the coil correspond with selective portions (e.g., inflection regions) of the secondary, complex shape. The coil adopts its primary shape during delivery through a catheter and its secondary shape after being released from the catheter.

In one embodiment, a method of using an embolic coil involves utilizing an embolic coil with larger and smaller diameter sections on the primary (or elongated, delivery) shape where the larger diameter sections correspond to selective portions (e.g., inflection regions) of the secondary (or delivered, unrestrained) shape. The embolic coil is tracked through a microcatheter and is used to fill an aneurysm where the coil's properties help minimize jumps or kicks during delivery of the embolic coil.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
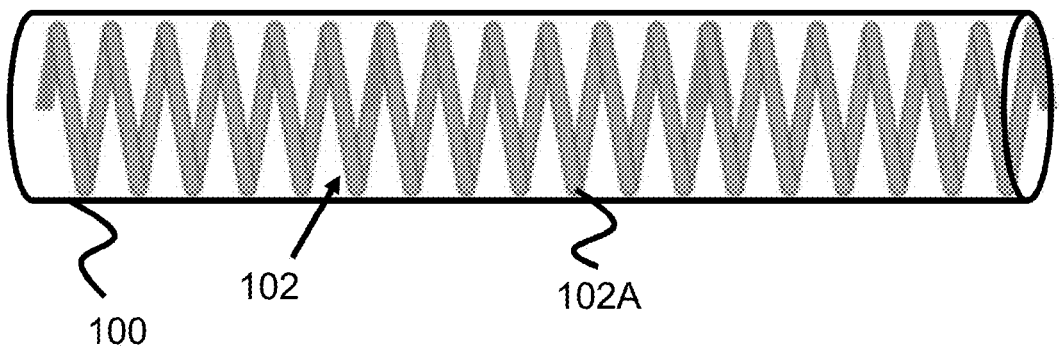
FIG. 1 illustrates a primary-wind embolic coil shape with a consistent diameter.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Embolic coils are generally used for occlusive purposes in the vasculature and are used in a variety of procedures including occluding aneurysms, vessel shutdown, fallopian tube occlusion, as well as occlusion for various other purposes. Depending on the geometry of the target therapeutic area and how the coil is being used, different secondary shapes may be desirable. For some needs—including occlusion of aneurysms—the coils are wound into a three-dimensional pattern to augment their occlusive effect when placed in the relatively confined space of the aneurysm sac.

The coils are generally wound a first time to achieve their primary shape (i.e., the coil in its elongated configuration), and a second time to achieve their secondary shape (i.e., the loops and curves formed when the coil is unrestrained). First, a wire composed of a super elastic, shape-memory material (e.g., NiTinol) is wound over a tubular mandrel with a consistent diameter, forming a plurality of helical loops (i.e., the wire forms a single, elongated helix). Once wound, the wire is heat treated to impart the primary, helical shape to the shape-memory material.

FIG. 1 illustrates a typical coil 102 being delivered through a delivery catheter 100 where the coil 102 is in its primary shape. As seen, the wire forms a plurality of helical loops 102A that further forms a single elongated helix.

Figure 2A:
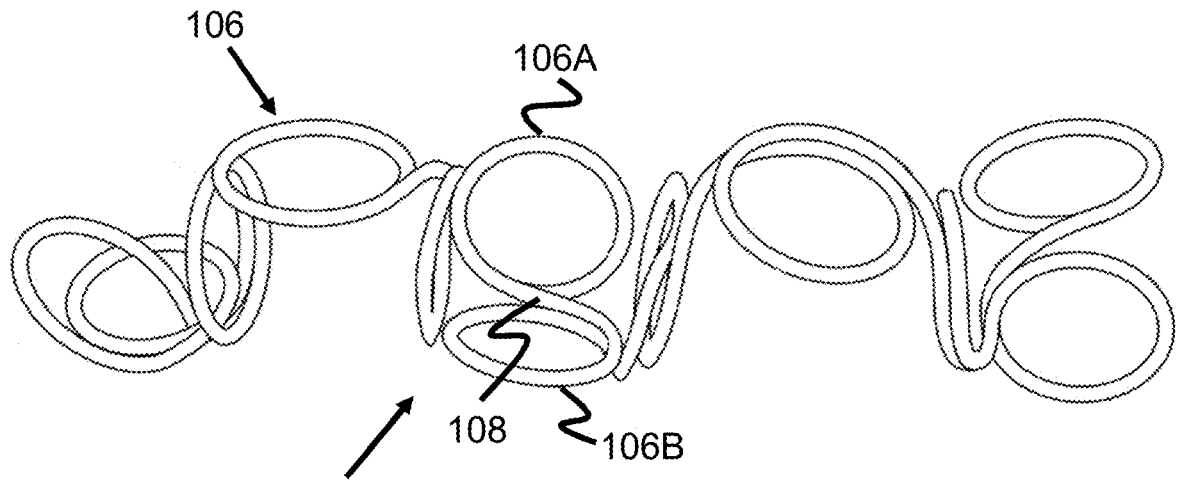
FIG. 2A illustrates a finished complex embolic coil shape shown after a secondary winding.
Figure 3:
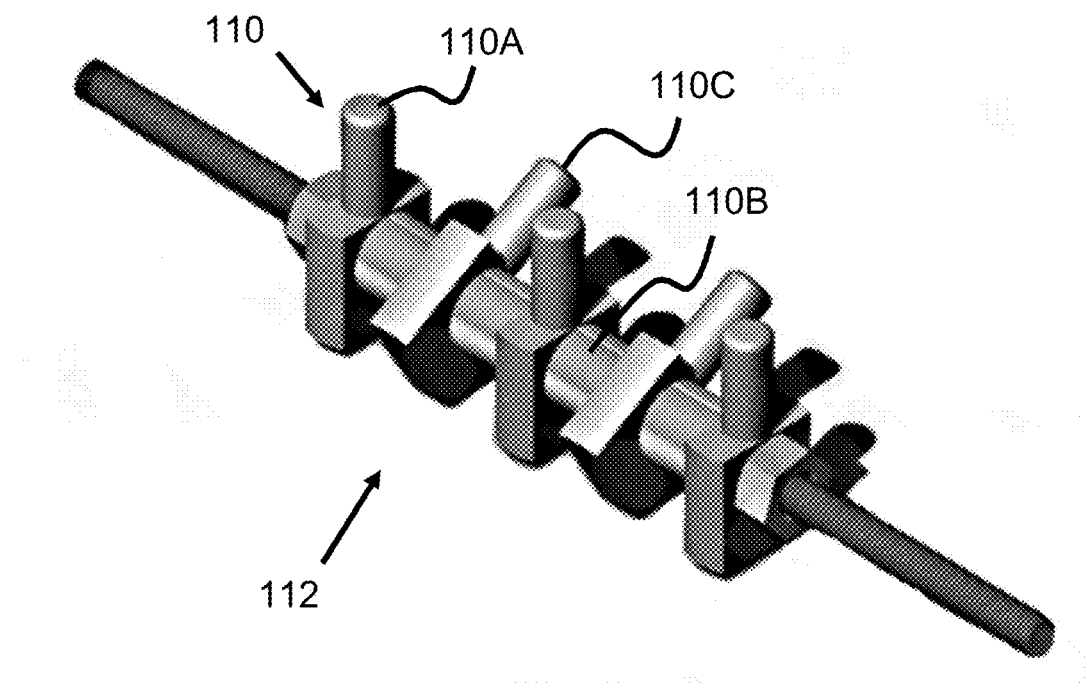
FIG. 3 illustrates a mandrel used to create a secondary wind shape on an embolic coil.

After the primary wind is imparted to the coil 102, a secondary shape is imparted to the coil 102 when unconstrained, as shown in FIG. 2A. The coil 102, after being given its primary wind (in its tubular shape with a plurality of helical windings 102A) is subsequently wound over a mandrel 112, as shown in FIG. 3, having a plurality of pins, posts, or shaped structures 110 onto which the coil 102 is looped to create various coil loops 106. The mandrel 112, for example, includes three vertical posts 110A (e.g., oriented at about 0 degrees), two posts 110C angled relative to the vertical posts 110A (e.g., at about 45 degrees relative to the posts 110A), and horizontal, cylindrical spacers 110B positioned between the posts 110A and 110C. The coil 102 can be wrapped around each of the posts/structures 110A, 110B, and 110C various numbers of times, in different directions, and at different angles. Complex coils, winding patterns, and winding techniques are further discussed in U.S. Pat. No. 9,089,405 which is hereby incorporated by reference in its entirety.

The complex secondary shape of coil 102 shown in FIG. 2A includes a plurality of loops 106 that are each connected to one or more adjacent loops 106. Where the coil 102 is looped around the same post (e.g. post 110A of the mandrel 112), these loops 106 are positioned on top of each other and continue the same wind direction (vertically adjacent loops). However, where the coil 102 continues around a different post (e.g. a loop wound on post 110A, followed by a loop wound on adjacent, radially offset/angled post 110C or spacer 110B) to create laterally adjacent loops, the direction the coil is wound changes to accommodate the radially offset or horizontal orientation of the adjacent post 110.

Figure 2B:
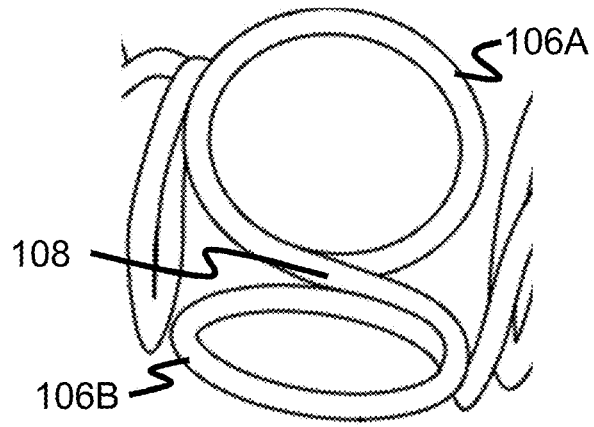
FIG. 2B illustrates a close-up view of the finished complex embolic coil shape of FIG. 2A, illustrating the sequential windings comprising the finished complex embolic coil shape.

This change in wind-direction results in transition or inflection regions that are created since the wind pattern of the coil is changing in these localized regions. For example, in FIGS. 2A and 2B, a first loop 106A is connected to adjacent loop 106B at about 90 degrees relative to each other, creating an inflection region 108. These inflection regions 108 may be considered high-stress/high-energy regions since the coil wind pattern is more abruptly changed or curved relative to the larger curves of the loops 106 of the coil 102. These inflection regions 108 affect the coil delivery process by causing sudden jumps or kicks to the delivery catheter 100 and the coil 102 as coil 102 is pushed from the delivery catheter 100. These jumps or kicks can make coil delivery difficult, both in terms of providing unwanted tactile feedback to the operator who is pushing the coil 102 and also potentially resulting in misplacement or migration of the coil 102 from the target area due to excessive delivery force.

One aspect of the present invention minimizes these jumps or kicks by increasing the coil flexibility in these inflection regions 108. Increasing the coil flexibility in these inflection regions 108 allows the coil 102 to adopt its secondary shape in a more uniform manner without the kicks/jumps that would otherwise be present.

Embolic coils 102 are coiled, as previously described, and therefore can act in a similar manner to a traditional spring. The stiffness of a spring is known as its k-value or spring constant. Factors affecting the k-value include wire diameter, primary wind diameter, shear modulus, and coil gap. A larger primary-wind diameter region would increase the flexibility and decrease the stiffness of the coil, while a smaller diameter coil would resist compression or extension—therefore augmenting stiffness while decreasing flexibility.

Figure 4:
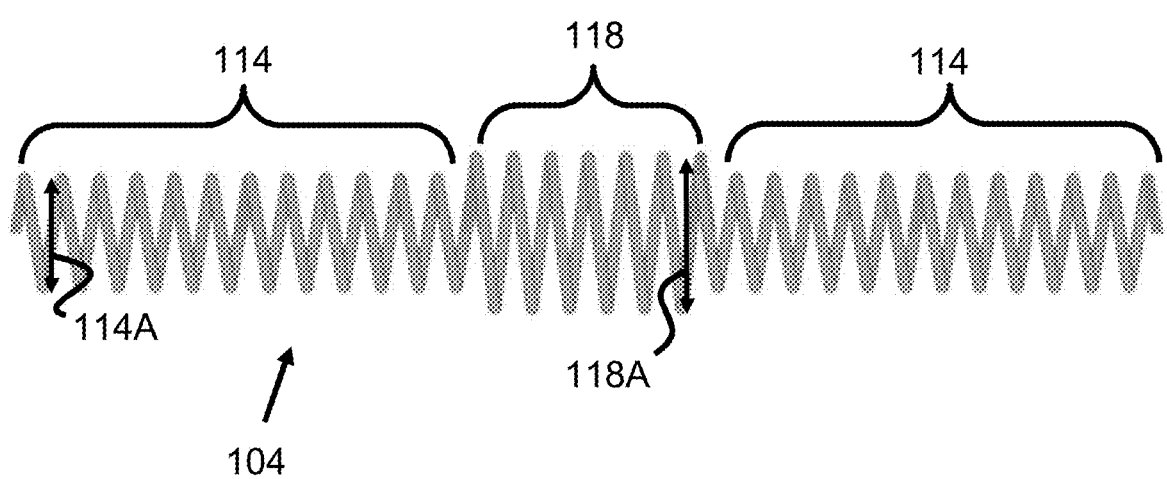
FIG. 4 illustrates a primary-wind embolic coil shape with smaller and larger diameter regions.

Utilizing a larger primary-wind diameter region along the secondary-shape inflection region therefore is one technique to increase flexibility and decrease stiffness of the embolic coil in these inflection regions 108. For example, FIG. 4 illustrates an embolic coil 104 having a plurality of smaller primary wind diameter regions 114 with a first diameter 114a and one or more larger primary wind diameter regions 118 with a second diameter 118a, larger than the first diameter 114a. Larger diameter regions 118, in one embodiment, are positioned at locations along the coil 104 that correspond to the inflection region regions 108 of a secondary, complex shape (e.g., shown in FIG. 2A), augmenting flexibility and decreasing stiffness within these inflection regions 108. Hence, the kicks and jumps associated with deploying the coil delivery 104 is mitigated as these inflection regions 108 create a gentler transition between loops.

Figure 5:
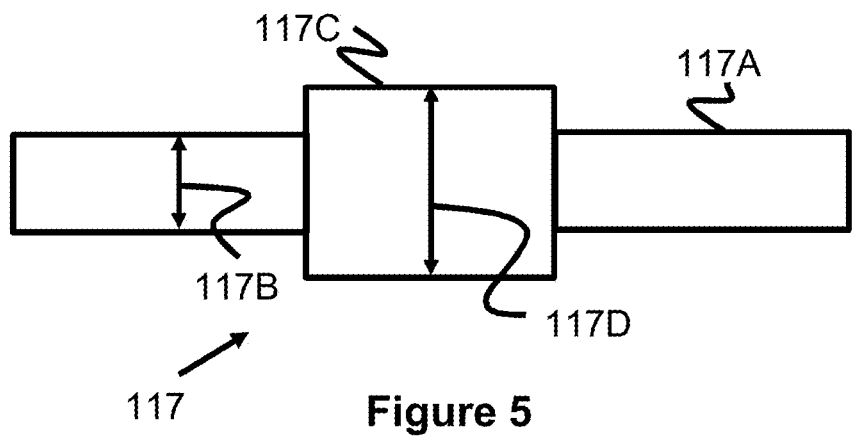
FIG. 5 illustrates a mandrel used to create a primary-wind embolic coil shape with smaller and larger diameter regions.

The primary wind shape of the coil 104 can be created with the mandrel 117 shown in FIG. 5, having a plurality of smaller diameter regions 117A and larger diameter regions 117C. The smaller diameter regions 117A have a diameter 117B that, when wire is wound on them, creates a coil region 114 having an outer diameter 114A (FIG. 4). Similarly, the larger diameter regions 117C have an outer diameter 117D that creates a coil region 118 having an outer diameter 118A. The wire of the coil 103 is wound over the regions 117A and 117C of the mandrel 117 and heat-set to create the desired primary shape.

The placement of the larger diameter regions 118 can be calculated by determining the length of coil necessary for a desired diameter loop (e.g., a loop circumference) or plurality of loops if multiple loops are stacked on each other. The length of the larger diameter regions 118 can be calculated by determining a distance between two adjacent loops. Hence, when the coil 104 is wound on a secondary-shape mandrel 112, the larger diameter regions 118 align between each of the loops created with regions 114. Alternately, a secondary-shape mandrel 112 can be configured to accommodate a coil 104 with predetermined intervals of the regions 114, 118 such that regions 118 are positioned between the loops.

Since longer lengths of the larger diameter regions 118 provide increasing flexibility, different lengths may be desirable based on the structure and function of the coil 104. For example, in some configurations it may desirable that the larger diameter region 118 extends along only a fractional portion of a length of the coil 104 that transitions between adjacent loops, thereby providing less flexibility. In other configurations, it may be desirable that the larger diameter region 118 extends the entire transition distance between adjacent loops or even beyond the transition distance between adjacent loops (i.e., partially forming a curve of the loops), providing increased flexibility.

Figure 6:
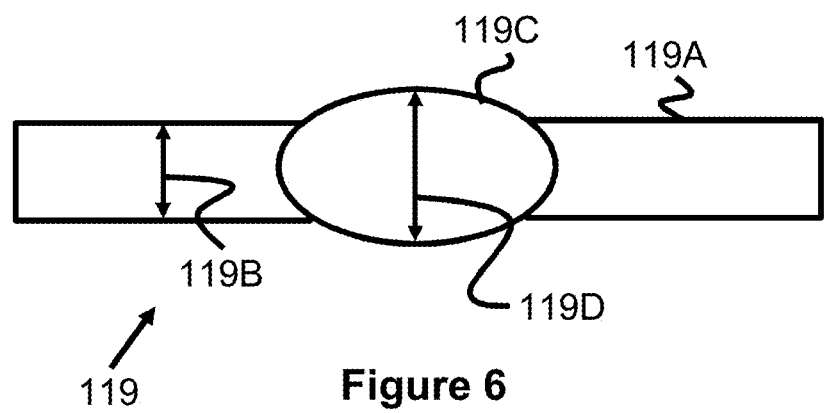
FIG. 6 illustrates a mandrel used to create a primary-wind embolic coil shape with smaller and larger diameter regions, where the larger diameter region of the mandrel has an elliptical shape.

Another embodiment of a mandrel 119 used for the primary wind shape of coil 104 shown in FIG. 4 is shown in FIG. 6—this figure shows a tapered or ovoid shaped region 119C having a larger diameter 119D relative to the diameter 119B of the smaller diameter regions 119A. The tapered or ovoid region 119C could be used to create a tapered enlarged diameter region 118. However, other enlarged region shapes are also possible, such as sinusoidal or an incrementally stepped cylindrical shape.

Two example datasets are provided below to illustrate how the outer diameter of both the larger diameter region 118 and the smaller diameter region 114 can be adjusted to increase or decrease flexibility. While these example ranges are illustrated, other k-values, filar, and outer diameters are also possible in accordance with the present invention. Specifically, Example 1 illustrates an embolic coil composed of wire having a diameter of 0.0015 inch that forms a primary coil shape with an outer diameter between 0.01 inch and 0.014 inch and a k-value range between 0.95 and 0.35. Example 2 illustrates an embolic coil composed of wire having a diameter of 0.00175 inch that forms a primary coil shape with an outer diameter between 0.01 inch and 0.014 inch and a k-value range between 2.05 and 0.75. In one specific example, an embolic coil 104 may be composed of either 0.0015 inch diameter wire or 0.00175 inch diameter wire, the smaller diameter region 114 forms primary coil loops with an outer diameter of 0.01 inch, and the larger diameter region 118 forms primary coil loops with an outer diameter of 0.014 inch. Alternately, the previous example may have primary coil loops in the larger diameter region 118 that progressively increase and then progressively decrease between the outer diameter values of 0.01 inch and 0.014 inch (e.g., created on previously-described mandrel 119). Please note, the following k-values are for coils with no gaps in between the coil windings (i.e., one loop abutting the next loop when the coil is in its primary shape), however the principles of the invention can also be applied to create a coil with gaps between windings—where the k value would be effected due to the gapped nature of the coil.

Example 1

| k-value (pounds/inch) | Filar (inches) | Outer Diameter (inches) |
| --- | --- | --- |
| 0.95 | 0.0015 | 0.01 |
| 0.82 | 0.0015 | 0.0105 |
| 0.71 | 0.0015 | 0.011 |
| 0.62 | 0.0015 | 0.0115 |
| 0.55 | 0.0015 | 0.012 |
| 0.49 | 0.0015 | 0.0125 |
| 0.43 | 0.0015 | 0.013 |
| 0.39 | 0.0015 | 0.0135 |
| 0.35 | 0.0015 | 0.014 |

Example 2

| k-value (pounds/inch) | Filar (inches) | Outer Diameter (inches) |
| --- | --- | --- |
| 2.05 | 0.00175 | 0.01 |
| 1.77 | 0.00175 | 0.0105 |
| 1.54 | 0.00175 | 0.011 |
| 1.35 | 0.00175 | 0.0115 |
| 1.19 | 0.00175 | 0.012 |
| 1.05 | 0.00175 | 0.0125 |
| 0.93 | 0.00175 | 0.013 |
| 0.83 | 0.00175 | 0.0135 |
| 0.75 | 0.00175 | 0.014 |

To ease the removal of the embolic coil 104 from a primary-shape mandrel with a variable shape (such as the mandrels 117 or 119), the mandrel can be constructed such that one or more of its larger diameter regions can be reduced in diameter. For example, the enlarged diameter regions may be composed of radially expandable and retractable mesh. Alternatively, the mandrel could be formed of a breakable material (e.g. ceramic) where the mandrel is simply fractured (for example, with a hammer) once the coil is wound and heat set. Fracturable mandrels are described in US 2017/0224355, which is hereby incorporated by reference in its entirety.

An alternative method to create a coil which has a primary-wind shape including smaller and larger-diameter sections is to create separate coils of a consistent profile (e.g. one set of coils with a smaller diameter, and another set of coils with a larger diameter) and then connect these coils together in an alternating fashion (e.g. one smaller diameter segment, one larger diameter segment, another smaller diameter segment, another larger diameter segment, etc.) utilizing known methods such as welding or adhesives to connect adjacent segments together. Such a technique could be used to create the primary-wind shape shown in FIG. 4.

Another technique to augment coil flexibility is to decrease the diameter of the wire that forms the coil. While the previous embodiments discussed increasing the primary winding diameter of a coil to augment flexibility and reduce stiffness, decreasing the wire thickness or diameter in selective regions of the coil can also be used to increase flexibility and reduce stiffness. A thicker coil better resists compression or elongation than a thinner coil since more energy can be stored in a thicker coil which leads to increased resistance and stiffness when the coil undergoes any shape changes—therefore a thinner coil would result in a more flexible and less stiff coil.

Figure 7:
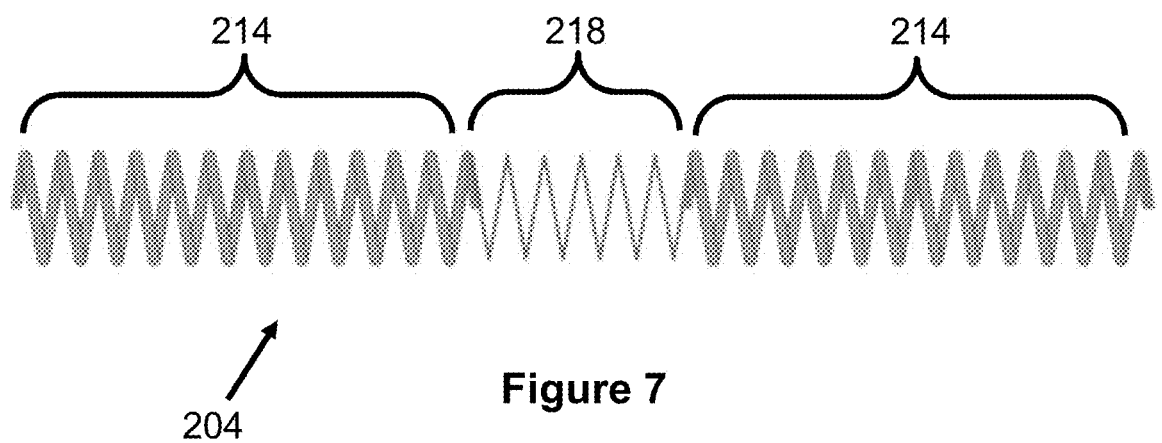
FIG. 7 illustrates a primary-wind embolic coil shape with thicker and thinner regions.

In this regard, selectively thinner regions can be included at the secondary shape inflection regions 108. This arrangement is shown in FIG. 7 in which the embolic coil 204 includes regions 214 composed of relatively thicker diameter wire and regions 218 composed of wire with a smaller diameter than that of region 214. The regions 214 having wire of a smaller diameter are positioned so as to coincide with the inflection regions 108 of the secondary wind to augment flexibility and reduce stiffness in the inflection regions 108.

These regions 214, 218 can be created in a number of ways, such as by selectively electro-polishing the wire of the coils at the inflection regions 108 either prior to forming the desired secondary shape or after forming the desired secondary shape. Alternatively, a coil comprising a thinner wire can be connected with a coil comprising a thicker wire in an alternating arrangement to create a unitary coil comprising the thinner wire and thicker wire regions. This approach of the thicker/thinner wires can also be used along with the approach described above utilizing augmenting primary wind diameter in selective regions, so that the coil inflection regions would utilize a larger primary wind diameter as well as a narrower wire diameter profile to further augment flexibility and decrease stiffness in the inflection regions of the coil's secondary shape.

In yet another embodiment, the wire of the inflection regions 108 can be formed from different materials that create greater flexibility than the materials of the wire forming the loops of the coil. Hence, the helical loops of the embolic coil can be relatively uniform while still providing greater flexibility in the inflection regions 108.

In another embodiment, the area within the helical loops of the embolic coil can be filled with a material to decrease flexibility. This material is positioned only within the areas of the coil that form its secondary shape loops, providing relatively reduced flexibility at the inflection regions 108 where no material is located. In one example, this material is hydrogel.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An embolic coil for delivery within a patient, comprising:
   a wire forming a primary shape of a helical coil; said helical coil further forming a secondary shape when unconstrained, comprising a first region forming a first loop and a second region forming a second loop; said first loop and said second loop being connected to each other by a third region;
   wherein said third region is more flexible than said first region forming said first loop and said second region forming said second loop; and,
   wherein said first loop is wound in a first direction and said second loop is wound in a second direction at about 90 degrees to the first loop; and wherein said third region creates an inflection point between said first loop and said second loop; and,
   wherein the helical coil contains hydrogel to decrease flexibility and wherein the inflection point is free from the hydrogel.

2. The embolic coil of claim 1, wherein said third region of said helical coil comprises helical loops of a first diameter and wherein said first region and said second region of said helical coil comprise helical loops of a second diameter that is less than said first diameter.

3. The embolic coil of claim 2, wherein said third region comprises wire of a first diameter and wherein said first region and said second region comprise wire having a second diameter that is larger than said first diameter.

4. The embolic coil of claim 2, wherein said primary shape of said helical coil is formed by winding wire on a mandrel having at least two different diameters.

5. The embolic coil of claim 1, further comprising a fourth region forming a third loop that is adjacent to said second loop and connected by a fifth region.

6. The embolic coil of claim 1, wherein the third region has been electropolished to increase flexibility.

7. An embolic coil system for treatment within a patient, comprising:
   a delivery device;
   an embolic coil comprising a wire forming a primary shape of a helical coil and further forming a secondary shape when unconstrained from said delivery device;
   said secondary shape comprising an inflection region between each of a plurality of laterally adjacent loops;
   wherein each of said inflection regions are more flexible than each of said plurality of laterally adjacent loops;
   wherein at least two of said plurality of laterally adjacent loops are wound in different directions relative to each other and at about 90 degrees relative to each other;
   further comprising hydrogel located within the helical coil; wherein the inflection regions are free from hydrogel.

8. The embolic coil of claim 7, wherein said inflection regions are composed of a plurality of helical loops having a first diameter, and wherein said plurality of laterally adjacent loops are composed of helical loops having a second diameter that is smaller than said first diameter.

9. The embolic coil of claim 8, wherein said wire has a first diameter in said inflection regions and said wire has a second diameter, larger than said first diameter, in said plurality of laterally adjacent loops.

10. The embolic coil of claim 7, wherein said wire has a first diameter in said inflection regions and said wire has a second diameter, larger than said first diameter, in said plurality of laterally adjacent loops.

11. The embolic coil of claim 7, wherein said delivery device is a microcatheter.

12. The embolic coil of claim 7, wherein the inflection regions have been electropolished to increase flexibility.

* * * * *